United States Patent [19]

Sharma et al.

[11] 4,131,626

[45] Dec. 26, 1978

[54] PROCESS FOR PRODUCING BROMINE

[75] Inventors: Lakshmi P. Sharma, Manlius; Bruce E. Kurtz, Marcellus, both of N.Y.

[73] Assignee: Allied Chemical Corporation, Morris Township, County of Morris, N.J.

[21] Appl. No.: 753,169

[22] Filed: Dec. 21, 1976

[51] Int. Cl.$^2$ ............................................ C07C 17/00
[52] U.S. Cl. .................................. 260/658 R; 423/502
[58] Field of Search .......................... 260/658 R, 660; 423/502, 332, 331

[56] References Cited

U.S. PATENT DOCUMENTS

| | | | |
|---|---|---|---|
| 677,906 | 7/1901 | Van Denbergh | 423/332 |
| 1,377,601 | 5/1921 | Ravner | 423/332 |
| 2,395,314 | 2/1946 | Blumer | 260/660 |
| 3,446,589 | 5/1969 | Botton et al. | 423/502 |
| 3,561,923 | 2/1971 | Takakura et al. | 423/502 |
| 3,641,172 | 2/1972 | Johnson et al. | 260/658 R |
| 3,812,211 | 5/1974 | Johnson | 260/658 R |
| 3,914,327 | 10/1975 | Johnson | 260/658 R |

FOREIGN PATENT DOCUMENTS 1066469  4/1967  United Kingdom ...................... 423/332

OTHER PUBLICATIONS

Comptes rendus 102, 1164–1167 (1886), Gorgeu.

*Primary Examiner*—Delbert E. Gantz
*Assistant Examiner*—Joseph A. Boska
*Attorney, Agent, or Firm*—Robert J. North; Anthony J. Stewart

[57] ABSTRACT

A process is described for producing bromine which comprises heating a bromide salt at a temperature of about 500° to 1000° C in the presence of an oxygen-containing gas, silicon dioxide and an oxidation catalyst preferably selected from the group consisting of $B_2O_3$, CaO, $Fe_2O_3$, $Al_2O_3$, $Na_2B_4O_7$, ZnO, MgO, $MnO_2$, $TiO_2$, $NaNO_2$ and mixtures thereof. A by-product silicate can optionally be formed which is useful in the glass industry.

The process is useful in many industrial applications, especially in the formation of ethylene dichloride, an intermediate used in the manufacture of vinyl chloride monomer, which involves reacting ethylene with bromine to produce ethylene dibromide, reacting the ethylene dibromide with a chloride salt to produce ethylene dichloride and a bromide salt, and oxidizing the bromide salt to bromine for reaction with ethylene to complete the cycle.

22 Claims, No Drawings

PROCESS FOR PRODUCING BROMINE

BACKGROUND OF THE INVENTION

1. Field of the Invention

This invention relates to the production of bromine by the oxidation of bromide salts in the presence of silicon dioxide and inorganic oxidation catalysts at high temperature, which is a useful process step in the production of ethylene dichloride.

2. Brief Description of the Prior Art

Processes are well known in the art for producing bromine from bromide salts such as the electrolysis of brine solutions containing bromide salts or subjecting the brine solution to gaseous chlorine in which chlorine oxidizes the soluble bromide salts to bromine.

The disadvantages of producing bromine from aqueous solutions of bromide salts by electrolysis are the cost of required electricity plus the complex electrolysis apparatus that is required, and the disadvantages in producing bromine from the chlorine oxidation of bromide salts are the use of highly toxic chlorine plus the difficulty in obtaining product bromine which is not contaminated with hydrochloric acid, hydrobromic acid or chlorine.

A proces is described in British Pat. No. 930,341 (1963) for converting aqueous hydrobromic acid to bromine by oxidation with a stream of air in the presence of a copper or iron catalyst. This method has the disadvantage of requiring the acidification of aqueous solutions of bromide salts prior to oxidation and also does not allow the oxidation to be carried out on solid bromide salts.

It is known that elemental bromine can be produced from heating a mixture of potassium bromide and clay comprised of aluminum silicate as exemplified in A. Gorgeu, Comptes rendus 102, 1164–7 (1886). However, the yields are not stated and the use of an aluminum silicate clay does not produce a by-product silicate such as sodium/calcium silicate that is useful in the glass industry, and which would render the process more economical.

A process is known in the prior art for producing alkali metal hydroxides by heating a mixture of an alkali metal salt, sand and phosphoric acid or boric acid with steam, as disclosed in The Chemical Trade Journal and Chemical Engineer, page 102 (Aug. 7, 1936); however, the process is not suitable for producing bromine.

Attempts in the prior art have been unsuccessful for developing a procedure which will produce high yields of bromine and by-product silicates useful in the glass industry by heating alkali metal bromides in the presence of silicon dioxide at high temperature, as disclosed by C. F. Schoenbein, Annalen der Physik 78, 513–23 (1849), where only a trace of bromine was formed under the conditions of the reaction.

Thus, a process is desired for converting solid bromide salts to bromine in high yield in the presence of silicon dioxide, which does not require mineral acids, electrolysis or the use of chlorine gas, and wherein a by-product silicate is formed which is useful in the glass industry.

SUMMARY

According to this invention a process is provided for producing bromine from bromide salts which comprises heating a bromide salt at a temperature of about 500° to 1,000° C in the presence of an oxygen-containing gas, silicon dioxide and an oxidation catalyst preferably selected from the group consisting of $B_2O_3$, $CaO$, $Fe_2O_3$, $Al_2O_3$, $Na_2B_4O_7$, $ZnO$, $MgO$, $MnO_2$, $TiO_2$, $NaNO_2$ and mixtures thereof.

There is also provided a process for producing ethylene dichloride from ethylene which comprises (a) reacting ethylene and bromine to form ethylene dibromide; (b) reacting the ethylene dibromide from step (a) with a chloride salt to produce ethylene dichloride and a bromide salt; and (c) oxidizing the bromide salt produced in step (b) to produce bromine which is then recycled for use in step (a) to constitute a cyclic process.

DESCRIPTION OF THE INVENTION AND THE PREFERRED EMBODIMENTS

The process of this invention involves the oxidation of bromide salts to bromine using an oxygen-containing gas in the presence of silicon dioxide and oxidation cataysts at a temperature of about 500° to 1000° C. The process obviates the need for complex electrochemical equipment, as in electrolysis, and also the use of hazardous and toxic chlorine as an oxidizing agent. Not only is bromine produced in high yield from this process, but also a sodium silicate by-product can be produced which is useful as a raw material in the glass industry.

The process of the invention can be exemplified by the following equations:

where M is an alkali metal of the Group I series of the periodic table such as lithium, sodium and potassium, Q is an alakline earth metal of the Group II series of the periodic table such as calcium, strontium, barium and magnesium.

The process involves heating solid bromide salts, especially those of the alkali and alkaline earth metals, with silicon dioxide, $SiO_2$, oxidation catalysts, such as calcium oxide and boron oxide, and oxygen-containing gas at a temperature of about 500° to 1,000° C. High yields of bromine are produced and a useful by-product silicate is obtained. When heating an alkali metal bromide or alkaline earth metal bromide at a temperature of about 500° to 1,000° C. with silicon dioxide and oxidation catalyst in a stream of an oxygen-containing gas, the production of bromine competes with two other undesirable processes, namely, the volatilization of the molten bromide salt above its melting point and "sintering" of the mixture, both of which tend to lower the overall yield of bromine.

Volatilization is a competing process in which the molten bromide salt is volatilized and carried away in the stream of oxygen-containing gas before oxidation can occur, thus lowering the yield of the oxidation, unless the volatilized bromide salt is recovered and returned to the process, which can be accomplished by suitable design of the apparatus.

"Sintering" of the mixture can occur at temperatures in the region of 900° to 1000° C and is the process whereby amorphous-like regions of the silicon dioxide-bromide salt mixture are produced in which formerly porous solid aggregates of the bromide salt become plugged because of the fact that they are now embedded in a thick amorphous medium into which oxygen cannot penetrate and thus, the yield of oxidation is lowered.

It has been found that by using a mixture of the bromide salt with silicon dioxide and oxidation catalysts, high yields of product bromine are obtainable when heating the mixture in a stream of oxygen-containing gas at 500° to 1000° C, whereby sintering of the reaction mixture and volatilization of the bromide salt are greatly decreased. This is especially evident in the temperature range of 900° to 1000° C where sintering occurs to a large extent unless oxidation catalysts such as calcium oxide and boron oxide are added in certain proportions.

The types of bromide salts which are applicable in the instant invention are preferably the bromides of the alkali or alkaline earth metals, such as lithium bromide, sodium bromide, potassium bromide, rubidium bromide, cesium bromide, beryllium bromide, magnesium bromide, calcium bromide, strontium bromide and barium bromide. Other bromide salts, such as those of copper, iron, lead, tin, antimony and the like, can also be used. Use of this invention can be made especially in those processes involving large amounts of waste or by-product bromide salts of the alkali and alkaline earth metals, which normally would be discarded, thus, resulting in pollution. Mixtures of different bromide salts can be used, but it is preferred in the process to use sodium bromide, potassium bromide or calcium bromide individually as the bromide salt, and it is particularly preferred to use sodium bromide.

The temperature at which the process is conducted is about 500° to 1000° C, preferably, 750° to 1000° C and more preferably, 875° to 975° C. In general, the temperature has to be at or above the melting point of the particular bromide salt being used, e.g. for lithium bromide, the melting point is 547° C; sodium bromide, 755° C; potassium bromide, 730° C; rubidium bromide, 682° C; cesium bromide, 636° C; beryllium bromide, 490° C; magnesium bromide, 700° C; calcium bromide, 765° C; strontium bromide, 643° C and barium bromide, 847° C. Temperatures above 1000° C are not desired because appreciable volatilization of the molten bromide occurs above this temperature, which tends to reduce the yield and efficiency of the process. The high heat of vaporization of the molten bromides removes a significant amount of heat from the reaction zone, thus, necessitating an additional heat input to compensate for this particular effect, and adds to the cost of the overall process.

The silicon dioxide, $SiO_2$, useful in this invention can be of any conventional type. Typical forms of silicon dioxide are sea sand, fused silica, ordinary glass, glassmaker's sand and crushed types of glass containing boron, sodium and/or aluminum silicates. It is preferred to use the silicon dioxide in a finely divided form so as to achieve an intimate mixture with the metal bromide and oxidation catalysts, and this is normally achieved by crushing the starting materials together, which can be accomplished by a number of suitable methods such as grinding in a mortar or pelletizing the mixture under pressure, and then grinding the pellets. However, it is preferred to use ordinary sea sand or glass makers sand, and glass makers sand is particularly preferred since it contains very few metal impurities such that when by-product silicate is formed from the process of this invention, it will not be significantly colored. The silicon dioxide serves two useful purposes in the reaction, (1) it forms a metallic silicate with the metallic oxide produced in the reaction, e.g. sodium silicate from sodium oxide, and (2) provides a supporting mass which helps to inhibit the bromide salt from volatilizing away from the reaction zone. In general, the molar ratio used of silicon dioxide to bromide salt is about 2:1 to 10:1 and preferably about 4:1 to 6:1.

Inorganic oxidation catalysts are a necessary part of the process and are preferably selected from the group consisting of boron oxide ($B_2O_3$), calcium oxide (CaO), iron oxide ($Fe_2O_3$), aluminum oxide, ($Al_2O_3$), borax ($Na_2B_4O_7$), zinc oxide (ZnO), magnesium oxide (MgO), manganese dioxide ($MnO_2$), titanium dioxide ($TiO_2$), sodium nitrite ($NaNO_2$), and mixtures thereof. Other inorganic oxidation catalysts are also applicable in the invention such as silver oxide, silver chromate, bismuth trioxide, chromic anhydride, ferric chloride, gold chloride, nitrogen oxide, sodium chromate, sodium perborate and the like.

In general, the oxidation catalyst is used in a total molar ratio of about 0.05:1 to about 4:1 of catalyst to bromide salt, wherein the catalyst may comprise a single compound or a mixture. It is preferred to use the catalysts CaO and $B_2O_3$ in combination, and especially in combination with NaBr, and in the molar ratios of CaO/NaBr of about 0.05:1 to 2:1 and $B_2O_3$/NaBr of about 0.05:1 to 2:1. Values of the molar ratio of CaO/NaBr of above 2:1 produce low yields of bromine and in the reaction at about 900° to 1000° C produce very small amounts of bromine in the initial stages of the reaction. Thus, molar ratios of CaO/NaBr below 2 are preferred and particularly of about 1.5:1 to 0.5:1. Molar ratios of $B_2O_3$/NaBr of about 0.3:1 to 0.5:1 are preferred.

Advantage can be taken of the fact that the by-product silicate of this invention can be used as a raw material in the manufacture of glass if sodium bromide is utilized to produce sodium silicate, which thus makes the process attractive economically and it is for this reason that primarily CaO and $B_2O_3$, which are components of high strength borosilicate glasses like Vycor ® (a trademark of Corning Glass Co.), are preferred and utilized.

The bromide salt, $SiO_2$, and the oxidation catalysts are ground together to form an intimate product mix which is then pelletized and optionally crushed into a powder, and then can either be charged into a vessel made of a ceramic or refractory material such as porcelain, and then heated in a horizontal tube reactor or the material charge can be used as a bed and heated in a vertical tube bed reactor or in a fluidized bed reactor. The charge, or product mix, can either be a powder made from crushed pellets or the charge can simply consist of pellets to avoid creating dust which could occur in the stream of oxygen-containing gas.

The oxygen-containing gas is comprised of about 1 to 100 volume percent of elemental oxygen and preferably of about 20 to 100 volume percent. It is preferred to use air containing about 20 volume percent of elemental oxygen. Other oxygen-containing gases that are applicable are pure oxygen and mixtures of air and oxygen. Air is particularly preferred in an industrial process because of its ease of handling, relatively low cost and reduced explosion hazard during operation. Small amounts of steam can also be optionally utilized in combination with the oxygen-containing gas, since it exerts a catalytic effect, and ozone can also be used in combination with the oxygen-containing gas.

The time required for completion of the reaction in a batch-wise process, to obtain good yields of bromine varies depending on the reactant concentration and the process apparatus design, but generally occurs in about 1 to 40 hours, and more preferably within about 4 to 20 hours and it is particularly preferred to choose the conditions such that about 4 to 8 hours is required which will give good yields of bromine.

The bromine produced by the process of this invention can be recovered by conventional techniques, such as by condensation.

The process of this invention for converting bromide salts to bromine is surprisingly applicable in a variety of industrial processes which utilize bromine as a starting reagent. An example is the process where bromine is reacted with ethylene to form ethylene dibromide which is commercially useful as the scavenger for lead in automobile gasolines containing tetraethyl lead.

Here, a cyclic process which involves converting ethylene to ethylene dibromide can be surprisingly constructed wherein bromide salts are first converted to free bromine by the process of this invention and then reacted with ethylene to form ethylene dibromide by known procedures in the art as exemplified in "Bromine and Its Compounds" by Jolles, Z. E., pp. 352–403, N.Y. Academic Press (1966) and Miller, S. A., "Ethylene and Its Industrial Derivatives", London, Benn. (1969). The cyclic process requires bromide salts, which can be by-product or waste bromide salts from other processes, and ethylene and yields ethylene dibromide as the principal product.

Another cyclic process in which this invention surprisingly has applicability is in converting ethylene to ethylene dichloride, which is a useful intermediate in the synthesis of vinyl chloride monomer. Here, ethylene dibromide, which is formed by the reaction of ethylene with bromine as discussed above, is reacted with a chloride salt in an aqueous system to produce ethylene dichloride, by a halogen exchange reaction, and a bromide salt. This reaction is known in the art and is exemplified in U.S. Pat. No. 3,641,172 (Johnson to Continental Oil Company, 1972) in which the halogen exchange reaction is greatly enhanced by the use of a cationic transfer agent such as a quaternary ammonium or phosphonium salt which assists in the migration of chloride ion into the organic ethylene dibromide layer. After the exchange reaction is completed, the aqueous solution of bromide salt, formed during the halogen exchange reaction, is evaporated to dryness yielding solid bromide salt which is oxidized to bromine which is subsequently reacted with ethylene to form ethylene dibromide, which is recycled to the halogen exchange step to complete the cycle.

A significant aspect of this process is in the fact that use can be made of many waste liquors containing chloride salts of the alkali metals, alkaline earth metals, Group VIII, IB, and IIB metals of the periodic table, which would otherwise be discarded leading to possible pollution. An example of such a waste liquor is that produced from the manufacture of synthetic soda ash, which is called distiller waste liquor which contains about 10.46% calcium chloride and 4.5% sodium chloride. The process also has the advantage of producing by-product sodium/calcium silicates, containing inorganic components such as boron, that are attractive as raw materials in the manufacture of glass.

The oxidation of the bromide salt in the cyclic process can alternatively be accomplished by electrolysis or oxidation with chlorine.

Details of apparatus and process engineering for such processes will be obvious to one skilled in the art.

The following examples are intended for illustrative purposes only and are not to be construed as limitations upon the scope or spirit of the instant invention. Parts in the examples are by weight unless otherwise indicated.

EXAMPLE 1

Apparatus

The apparatus used was a vertical packed bed reactor tube of ⅜ inch I.D. and 30 inches long, made of Vycor ® glass (a trademark of Corning Glass Co.) or pure aluminum oxide. It was outfitted with an inlet tube at the bottom for the entry of oxygen-containing gas, and at the top with an inlet for a thermocouple to measure the temperature and an outlet at the top leading to bromine scrubbers for the collection and quantitative determination of produced bromine. The reactor tube was surrounded by 18 inch long circular heaters for heating the samples. The bottom 9 inches of the reactor tube was filled with saddle-shaped pieces of broken ceramic packing material called Berl saddles, which are about ⅛ inch by ⅛ inch pieces in size and are used as a refractory material. The next 10 inches of the reactor tube was filled with a sample of sodium bromide, $SiO_2$, and the inorganic catalysts, $CaO$ and $B_2O_3$. The charge was made by mixing the sodium bromide, $SiO_2$, and oxidation catalysts together to form an intimate powder, and then pelletizing the powder using a die of ⅜ inch diameter under 24,000 psig pressure. The produced pellets were either used as is or were further crushed into a granular powder. The thermocouple was inserted vertically into the bed through the sample until it touched the top of the layer of Berl saddles. The heaters were adjusted so that the packed bed was about 5 inches from the bottom of the reactor tube so that the oxygen-containing gas could be preheated before entering the packed bed for reaction. Air or oxygen was passed through the reactor tube during the reaction at the rate of about 190 cc./minute, the temperature was in the range of about 750° to 1000° C, and the bromine produced during the course of the reaction was absorbed in 5 N sodium hydroxide solution in the scrubbers and titrated for quantitative determination with sodium thiosulfate. The samples after cooling were weighed to determine weight loss.

Procedure

A charge of 59.7 parts crushed borosilicate glass (¼ inch by ⅛ inch pieces) and broken pellets (¼ inch by ⅛ inch) made from 41.3 parts sodium bromide (0.4 mols), 11.2 parts calcium oxide (0.2 mols), and 36.1 parts $SiO_2$ (sea sand, 0.6 mol) was placed in the vertical reactor tube and heated at about 950° C for 39½ hours under a flow of entering oxygen gas at a flow rate of 190 cc per minute at 70° F. The bromine produced was collected in a solution of 5 N sodium hydroxide and titrated using a standard titration technique indicating that 22.43 parts bromine (32 parts theory) representing a 70 percent yield of theory of bromine had been produced.

EXAMPLE 2

A statistically designed set of experiments composed of 57 runs was run using the Plackett-Burnam approach as described by Isaacson, W. B. in Chemical Engineering, page 69 (1973), "Statistical Analysis for Multivariate Systems," and utilizing the apparatus and procedure described in Example 1. The variables that were studied were: temperature, at 950° C, 900° C, 850° C, 750° C, 650° C; use of steam with oxygen versus oxygen alone; various molar ratios of silicon dioxide to sodium bromide of 0.5:1, 1:1, 1.5:1 and 2:1; types of silicon dioxide, either ordinary sea sand or glass makers sand; calcium oxide as a catalyst in calcium oxide/sodium bromide molar ratios of 0, 0.05:1, 1:1; powdered sodium borosilicate glass as a catalyst in ratios of glass to sodium bromide in parts by weight of 2.9:1 and 0; the use of boron oxide as a catalyst in boron oxide/sodium bromide molar ratios of 0 and 0.025:1; use of iron oxide as a catalyst in iron oxide/sodium bromide molar ratios of 0 and 0.025:1; and the particle size of the sample either as pellets or in powder form. The experiments were conducted using a fixed charge of sodium bromide (0.5 mol), a fixed flow rate of oxygen at 300 cc. per minute at 70° F, and each experiment was run for about 6 hours. The data from the runs were examined statistically and the following trends were found: (1) high molar ratios of calcium oxide to sodium bromide had a deleterious effect on sodium bromide oxidation at 950° C; (2) high molar ratios of silicon dioxide to sodium bromide coupled with small molar ratios of boron oxide to sodium bromide increased the bromide oxidation rate by a factor of about 10 to 20 versus lower molar ratios of silicon dioxide to sodium bromide in the absence of boron oxide; (3) the effects of steam increased the amount of bromide oxidation in one case; (4) the presence of crushed sodium borosilicate glass and iron oxide had significant effects in increasing the rate of bromide oxidation; (5) combinations of small amounts of calcium oxide and boron oxide containing higher silicon dioxide to sodium bromide molar ratios significantly increased the rate of oxidation of bromide salt to bromine at 750° and 850° C; and (6) higher temperatures were significant in producing higher yields of bromine.

EXAMPLE 3

This example illustrates runs which were made based upon the trends and results obtained in Example 2 to maximize the yield of bromine, to decrease required reaction time in obtaining a high yield, to determine the necessary reaction conditions for using glass makers sand such that a suitable by-product sodium silicate could be produced which would be useful to the glass industry. Runs were made in the apparatus described in Example 1 except the apparatus was horizontal rather than vertical, and smaller charges were heated in a ceramic boat container. The $SiO_2$/NaBr and $B_2O_3$/NaBr molar ratios were kept constant at 4:1 and 0.4:1, respectively, and air was used at a flow rate of 300 cc. per minute at 70° C. The variables that were tested were temperature, time, and calcium oxide/sodium bromide molar ratios. Two typical runs selected from the following Table are described as follows:

A. (Run 31) A mixture of 1.5034 parts sodium bromide, 3.5031 parts of glass makers sand ($SiO_2$), 0.4087 parts boron oxide and 1.6345 parts calcium oxide were mixed together to form a powder of $-200 + 325$ Tyler mesh size and pelletized and the pellets were then crushed into about ¼ inch by ¼ inch granules. The granules were placed in a ceramic boat and placed into the horizontal tube reactor. A flow rate of air at 300 cc. per minute at 70° F was introduced into the tube and the charge heated at 900° C for 4 hours. Titration determined that 4.3 weight percent of sodium bromide had been oxidized to bromine, while 73.8 weight percent of sodium bromide had volatilized during the reaction.

B. (Run 36) A mixture of 1.6648 parts sodium bromide, 3.8803 parts of glass makers sand ($SiO_2$), 0.4527 parts of boron oxide and 0.9055 parts of calcium oxide were mixed and pelletized as described in procedure A. The charge was placed in a ceramic boat and heated in a horizontal tube reactor at 900° C for about 7 hours using the flow rate of air as described in procedure A. Analysis showed that 76.0 weight percent of the sodium bromide had been oxidized to free bromine and 7.7 weight percent of sodium bromide had volatilized under the conditions of the reaction.

The following table lists the different runs that were made using the same procedure of A and B in which about 1.3 to 1.6 parts of sodium bromide were used and fixed molar ratios of silicon dioxide to sodium bromide and boron oxide to sodium bromide of 4:1 and 0.4:1, respectively, were used, and a flow rate of air of about 300 cc. per minute at 70° F was maintained.

TABLE

| Run | Type of $SiO_2$ | Molar Ratio of CaO/NaBr | Time Hrs:Min. | Temp. | Wt. % of NaBr oxidized to $Br_2$ | Wt. % of NaBr volatilized |
|---|---|---|---|---|---|---|
| 1 | Glass Maker's Sand | 2:1 | 5:51 | 1000° C | <2 | >92 |
| 2 | " | " | 3:49 | " | <2 | >92 |
| 3 | " | " | 7:52 | " | <2 | >92 |
| 4 | " | " | 1:51 | " | 7.4 | 91.8 |
| 5 | " | 1:1 | 5:51 | " | 37.6 | 40.0 |
| 6 | " | " | 3:51 | " | 23.5 | 53.9 |
| 7 | " | " | 1:53 | " | 39.6 | 43.4 |
| 8 | " | " | 7:52 | " | 38.2 | 46.2 |
| 9 | " | 0.5:1 | 2:07 | " | 50.1 | 36.3 |
| 10 | " | " | 4:24 | " | 51.3 | 41.9 |
| 11 | " | " | 6:11 | " | 51.4 | 45.9 |
| 12 | " | " | 7:31 | " | 49.1 | 49.1 |
| 13 | " | 0.1:1 | 5:17 | 950° C | 39.7 | 44.1 |
| 14 | " | " | 5:17 | " | 55.4 | 33.1 |
| 15 | " | 0.1:1 | 4:01 | 900° C | 52.8 | 36.2 |
| 16 | " | " | 4:01 | " | 56.4 | 25.2 |
| 17 | Crushed Sodium borosilicate glass | 2:1 | 2:06 | 1000° C | 21.4 | 78.2 |
| 18 | " | " | 4:24 | " | 56.3 | 43.3 |
| 19 | " | " | 6:11 | " | 17.0 | 43.3 |
| 20 | " | " | 7:31 | " | 47.7 | 51.9 |
| 21 | " | 1:1 | 1:00 | " | 60.0 | 29.0 |
| 22 | " | " | 2:01 | " | 59.4 | 31.6 |
| 23 | Crushed Sodium borosilicate glass | 1:1 | 4:03 | 1000° C | 64.6 | 28.7 |
| 24 | " | " | 7:11 | " | 61.5 | 34.5 |
| 25 | Glass | 0.1:1 | 1:00 | " | 32.5 | 55.3 |

TABLE-continued

| Run | Type of SiO$_2$ | Molar Ratio of CaO/NaBr | Time Hrs:Min | Temp. | Wt. % of NaBr oxidized to Br$_2$ | Wt. % of NaBr volatilized |
|---|---|---|---|---|---|---|
| 26 | Maker's Sand | " | 2:00 | " | 32.8 | 54.5 |
| 27 | " | " | 4:03 | " | 28.6 | 58.5 |
| 28 | " | " | 7:11 | " | 26.8 | 60.1 |
| 29 | " | 2:1 | 1:00 | 900° C | negligible | 31.3 |
| 30 | " | " | 2:00 | " | " | 32.6 |
| 31 | " | " | 4:00 | " | 4.3 | 73.8 |
| 32 | " | " | 7:03 | " | 8.2 | 89.5 |
| 33 | " | 1:1 | 1:00 | " | 66.7 | 7.7 |
| 34 | " | " | 2:00 | " | 70.5 | 8.3 |
| 35 | " | " | 4:00 | " | 75.1 | 7.4 |
| 36 | " | " | 7:03 | " | 76.0 | 7.7 |
| 37 | " | 0.5:1 | 1:00 | " | 59.9 | 10.5 |
| 38 | " | " | 2:00 | " | 71.3 | 5.4 |
| 39 | " | " | 4:00 | " | 72.6 | 6.8 |
| 40 | " | " | 7:42 | " | 71.9 | 8.6 |
| 41 | " | 0.1:1 | 1:00 | " | 57.3 | 11.9 |
| 42 | " | " | 2:00 | " | 61.1 | 14.7 |
| 43 | " | " | 4:00 | " | 69.2 | 19.3 |
| 44 | " | " | 7:42 | " | 68.5 | 23.7 |

EXAMPLE 4

This example illustrates the use of the bromide oxidation in a cyclic process for producing ethylene dichloride, an intermediate useful in preparing vinyl chloride monomer.

A. Bromination of Ethylene

Ethylene gas is passed into a water-cooled glass reactor containing liquid bromine. The ethylene dibromide formed is removed in a countercurrent manner to the incoming ethylene in order to remove dissolved bromine.

B. Halogen Exchange Reaction

The ethylene dibromide formed in Step A is added to an aqueous solution of chloride salt in which the molar ratio of ethylene dibromide to chloride salt is greater than one. A phase transfer catalyst such as methyltricaprylyl ammonium chloride is added and the mixture is stirred and heated to reflux.

The reflux is maintained for about 2 to 4 hours, and at the end of the reflux the organic portion of the mixture containing ethylene dichloride, chlorobromoethane and ethylene dibromide, is distilled leaving an aqueous solution of bromide salts. The mixture of ethylene dichloride, ethylene dibromide and bromochloroethane is further fractionated yielding pure ethylene dichloride which is stored for conversion to vinyl chloride monomer, and the bromochloroethane and ethylene dibromide are recycled back to react with the next batch of aqueous chloride salts in the halogen exchange reaction.

The aqueous solution of bromide salts is evaporated to dryness by heating and the solid bromide salt residue, is then oxidized to bromine by the general method of the invention as illustrated in Example 3 and the resulting bromine is then recycled to react with ethylene to form ethylene dibromide in step A to complete the cyclic process.

We claim:

1. A process for producing bromine from bromide salts which comprises heating a solid bromide salt at a temperature of about 500° to 1000° C in the presence of an oxygen-containing gas, silicon dioxide and an oxidation catalyst comprising a mixture of B$_2$O$_3$ and CaO.

2. The process of claim 1 wherein the oxidation catalyst further comprises a member selected from the group consisting of Fe$_2$O$_3$, Al$_2$O$_3$, Na$_2$B$_4$O$_7$, ZnO, MgO, MnO$_2$, TiO$_2$, NaNO$_2$ and mixtures thereof.

3. The process of claim 1 wherein the bromide salt is selected from the group consisting of the alkali metal and alkaline earth metal bromides and mixtures thereof.

4. The process of claim 3 wherein the bromide salt is sodium bromide.

5. The process of claim 1 wherein the molar ratio of silicon dioxide to bromide salt is about 2:1 to 10:1 and the molar ratio of catalyst to bromide salt is about 0.05:1 to 4:1.

6. The process of claim 5 wherein the catalyst is a mixture of B$_2$O$_3$ and CaO and the molar ratio of CaO to bromide salt is about 0.05:1 to 2:1.

7. The process of claim 1 wherein the temperature is about 750° to 1000° C.

8. The process of claim 1 wherein the temperature is about 875° to 975° C.

9. The process of claim 1 wherein the oxygen-containing gas is comprised of about 1 to 100 volume percent of elemental oxygen.

10. The process of claim 9 wherein the oxygen-containing gas is air.

11. In a process for producing ethylene dichloride from ethylene including the steps of: (a) reacting ethylene with bromine to form ethylene dibromide; (b) reacting the ethylene dibromide from step (a) with a chloride salt dissolved in an aqueous system to produce ethylene dichloride and a bromide salt; the improvement which comprises oxidizing the bromide salt produced in step (b) by heating the bromide salt in dry solid form at a temperature of about 500° to 1000° C in the presence of an oxygen-containing gas, silicon dioxide and an oxidation catalyst comprising a mixture of B$_2$O$_3$ and CaO to produce bromine which is then recycled for use in (a).

12. The process of claim 11 wherein the oxidation catalyst further comprises a member selected from the group consisting of FE$_2$O$_3$, AL$_2$O$_3$, Na$_2$B$_4$O$_7$, ZnO, MgO, MnO$_2$, TiO$_2$, NaNO$_2$ and mixtures thereof.

13. The process of claim 11 wherein the bromide salt is selected from the group consisting of the alkali metal and alkaline earth metal bromides and mixtures thereof.

14. The process of claim 11 wherein the bromide salt is sodium bromide.

15. The process of claim 11 wherein the molar ratio of silicon dioxide to bromide salt is about 2:1 to 10:1 and the molar ratio of catalyst to bromide salt is about 0.05:1 to 4:1.

16. The process of claim 15 wherein the catalyst is a mixture of $B_2O_3$ and CaO and the molar ratio of CaO to bromide salt is about 0.05:1 to 2:1.

17. The process of claim 11 wherein the temperature is about 750° to 1000° C.

18. The process of claim 11 wherein the temperature is about 875° to 975° C.

19. The process of claim 11 wherein the oxygen-containing gas is comprised of about 1 to 100 volume percent of elemental oxygen.

20. The process of claim 19 wherein the oxygen-containing gas is air.

21. The process of claim 1 wherein said silicon dioxide and said oxidation catalyst are present as borosilicate glass.

22. The process of claim 11 wherein said silicon dioxide and said oxidation catalyst are present as borosilicate glass.

* * * * *